United States Patent [19]

Metzger

[11] 3,965,090

[45] June 22, 1976

[54] AMPHOTERICIN COMPLEXES

[75] Inventor: Julio Metzger, East Brunswick, N.J.

[73] Assignee: E. R. Squibb & Sons, Inc., Princeton, N.J.

[22] Filed: Feb. 18, 1975

[21] Appl. No.: 550,313

Related U.S. Application Data

[60] Continuation-in-part of Ser. No. 338,122, March 5, 1973, abandoned, which is a division of Ser. No. 203,037, Nov. 29, 1971, abandoned.

[52] U.S. Cl............................ 260/210 AB; 424/181
[51] Int. Cl.$^2$................... A61K 31/71; C07G 11/00
[58] Field of Search............... 424/181; 260/210 AB

[56] References Cited

OTHER PUBLICATIONS

Schaffner et al., Antibiot. Chemotherapy, vol. vol. 11 (1961), pp. 724–732.

*Primary Examiner*—Sam Rosen
*Attorney, Agent, or Firm*—Lawrence S. Levinson; Merle J. Smith; Burton Rodney

[57] ABSTRACT

This invention relates to a new form of amphotericin B which comprises a complex of amphotericin B and succinic acid. This new form of amphotericin B is more active than amphotericin B itself and has the particular advantage of being soluble in acidic or alkaline solutions.

4 Claims, No Drawings

AMPHOTERICIN COMPLEXES

This application is a continuation-in-part of copending application Ser. No. 338,122 filed Mar. 5, 1973, now abandoned which is a division of application Ser. No. 203,037 filed Nov. 29, 1971, now abandoned.

BACKGROUND OF THE INVENTION

Amphotericin B is a polyene macrolide compound having antifungal properties. It is produced by cultivation of an organism and extracted from the culture. Amphotericin B is essentially a high molecular weight macrocyclic lactone, better known as a macrolide, possessing a chromophore of 7 conjugated double bonds. In addition to the large lactone nucleus, amphotericin B has other characteristic groups including an amino sugar. A general discussion of macrolide antibiotics is found in Kirk-Othmer, Encyclopedia of Chemical Technology, Second Edition, Volume 12, pp. 632 et seq., while a general discussion of polyene antibiotics is found in the same work, Volume 16, pp. 133 et seq.

While amphotericin B has been recognized as a valuable material, particularly in its powerful antifungal properties and in the apparent inability of fungus organisms to develop readily any strains or forms that are resistant to amphotericin B, its use has been limited by lack of adequate water solubility in forms of amphotericin B which are otherwise stable and appropriate.

Schaffner et al., Antibiotics and Chemotherapy, Vol. XI, No. 11, 724–732 disclose the preparation of N-acylamphotericin B, such as N-succinylamphotericin B, by reaction of succinic anhydride with a slurry of amphotericin B in methanol whereby the anhydride reacts with the amino groups of the amphotericin B. Although Schaffner et al indicate that certain of the N-acylamphotericin B exhibit increased solubility in organic solvents and that acidic derivatives, as their alkaline salts, exhibit true water solubility, unfortunately, it has been found that N-succinylamphotericin B has only about 2-3% of the in vitro bioactivity of the parent amphotericin B and such N-succinyl derivative has an in vivo bioactivity proportional to its in vitro activity. Accordingly, it is quite clear that the N-succinylamphotericin B is inferior in biological activity to the parent amphotericin B.

OBJECTS OF THE INVENTION

It is, accordingly, an object of the present invention to provide a more soluble form of amphotericin B which is at least as active as the parent amphotericin B, and preferably more active than the parent. A further object is to provide a method for preparing these new forms of amphotericin B. These and other objects of the present invention will be apparent from the following description.

DETAILED DESCRIPTION

This invention relates to a new soluble form of amphotericin B which is believed to be a complex of amphotericin B comprising amphotericin B and the anion of an organic mono- or polycarboxylic acid of up to 20 carbon atoms. Examples of such acids are acetic, oxalic, propanoic, malonic, 2-methylpropanoic, butanoic, succinic, 2,2-dimethylbutanoic, fumaric, citric, malic, glutaric, pentanoic, hexanoic, octanoic, nonoic, decanoic, hendecanoic, dodecanoic, palmitic, ricinoleic, oleic, stearic, or ethylenediaminetetraacettic acid.

This type of aphotericin B may be prepared by adding the organic carboxylic acid to a substantially anhydrous (not over about 1% water) alcoholic solution of amphotericin. Methanol is a preferred alcohol although any water soluble or partially water miscible alcohol may be used, such as ethanol, propanol or butanol. The mixture of amphotericin B and the organic carboxylic acid (containing excess acid, typically from about 0.5 to about 20 mols of acid per mol of amphotericin B) is agitated for a short time, typically from about 2 minutes to about 30 minutes, and the pH then adjusted to neutral. The mixture is then heated moderately to from about 35°C to about 65°C while mixing for a period of from about 0.5 to about 2 hours. The pH is then readjusted to neutral and the mixture cooled slowly over a period of from about 0.5 to about 4 hours. The solid is filtered and dried.

The amphotericin B complex of the present invention is soluble in water under both strongly acid and strongly alkaline conditions while exhibiting diminished solubility at neutral or near neutral pH. Maximum solubility of the amphotericin B complexes of the present invention occur at about pH 2 and at about pH 10. The complexes of the present invention are less soluble in methanol than amphotericin B. Forty mg of the complexes of the present invention are soluble in 750 ml of methanol whereas 100 mg of amphotericin B are soluble in 750 ml of methanol.

The following example illustrates the present invention without, however, limiting the same thereto. All temperatures in this application are expressed in degrees Centigrade unless otherwise indicated.

EXAMPLE

Amphotericin B-Succinic Acid Complex 42.64 g of amphotericin B containing 40.0 g activity are solubilized in 10.0 l of methanol by means of 7.0 ml of 5.8 N HCl. The solution is filtered.

To this solution is added a solution of 400 ml of methanol containing 40 g of succinic acid. The pH drops to 4.05 and is adjusted to 7.0 with 29.6 ml of concentrated ammonia. The crystal suspension which forms is heated to 45°–50°C, slurried for 60 minutes, cooled to room temperature over a 2-hour period, filtered and dried overnight at 45°–50°C.

The resulting crystalline complex weighs 34.2 g. This complex has a solubility in water of 28.0 g/l at pH 2. Amphotericin B, on the other hand, has a solubility in water of less than 1 gram/l at pH 2. The complex has an X-ray pattern and U.V. absorption at 405 millimicrons ($E_1^1$) in methanol of 1649; pure amphotericin B dissolved in methanol has a $E_1^1$ U.V. absorption value of 1800 at 405 millimicrons.

One hundred mg of this complex when added to 80 ml of methanol and the pH adjusted to 9.5 (with triethylamine) are soluble to the extent of 35%, whereas 100 mg of amphotericin B are completely soluble in 80 ml of methanol.

The above amphotericin B-succinic acid complex of the present invention has a biological activity of 1000–1250γ/mg while amphotericin B has a bioloiical activity of 920γ/mg.

The test method used in establishing the biological activity is that described by Platt et al., Analytical Microbiology, Volume II, Academic Press, 1972, editor F. Kavangh, 4.2 IV, pp. 163-170. The assay organism is Candida tropicalis, ATCC No. 13803.

What is claimed is:

1. A crystalline amphotericin B complex comprising about 1 mole of amphotericin B and from about 0.5 to about 20 moles of succinic acid, the complex having a solubility in water at pH 2 of about 28 grams per liter, and a U.V. absorption at 405 millimicrons ($E_1^1$) in methanol of 1649.

2. A method for preparing a crystalline amphotericin B complex which comprises reacting from about 0.5 to about 20 moles of succinic acid with one mole of amphotericin B, the resulting complex having a solubility in water at pH 2 of about 28 grams per liter, and a U.V. absorption at 405 millimicrons ($E_1^1$) in methanol of 1649.

3. The method as defined in claim 2, said process including the steps of adding from about 0.5 to about 20 moles of succinic acid per mole of amphotericin B to a substantially anhydrous alcoholic solution of amphotericin B, adjusting the pH to neutral, heating to a temperature of from about 35°C. to about 65°C. for a period of from about 0.5 to about 2 hours, adjusting the pH to neutral and cooling slowly over a period of from about 0.5 to about 4 hours.

4. The method as defined in claim 3 wherein said alcoholic solution comprises methanolic solution.

* * * * *

UNITED STATES PATENT AND TRADEMARK OFFICE
CERTIFICATE OF CORRECTION

PATENT NO. : 3,965,090
DATED : June 22, 1976
INVENTOR(S) : Julio Metzger

It is certified that error appears in the above—identified patent and that said Letters Patent are hereby corrected as shown below:

Column 1, line 68, "ethylenediaminetetraacettic" should read --ethylenediaminetetraacetic--.
Column 3, at the end of claim 2, insert --1649.--

Signed and Sealed this

Seventh Day of September 1976

[SEAL]

Attest:

RUTH C. MASON
*Attesting Officer*

C. MARSHALL DANN
*Commissioner of Patents and Trademarks*